United States Patent
Sanchez

(10) Patent No.: US 8,287,508 B1
(45) Date of Patent: Oct. 16, 2012

(54) USING MOISTURE-WICKING ARTICLE WRAPPED OVER OPENINGS IN AN ELONGATED URINE COLLECTING CONTAINER FOR DRAWING URINE FROM A REGION SURROUNDING AN URETHRAL OPENING

(76) Inventor: Robert A. Sanchez, Fallbrook, CA (US)

(*) Notice: Subject to any disclaimer, the term of this patent is extended or adjusted under 35 U.S.C. 154(b) by 201 days.

(21) Appl. No.: 12/840,475

(22) Filed: Jul. 21, 2010

(51) Int. Cl.
*A61M 1/00* (2006.01)
*A61F 5/44* (2006.01)

(52) U.S. Cl. ........ 604/319; 604/317; 604/322; 604/326; 604/346; 604/347; 604/349

(58) Field of Classification Search .................. None
See application file for complete search history.

(56) References Cited

U.S. PATENT DOCUMENTS

| | | | |
|---|---|---|---|
| 4,610,675 A | | 9/1986 | Triunfol |
| 4,650,477 A | * | 3/1987 | Johnson ................. 604/321 |
| 4,747,166 A | | 5/1988 | Kuntz |
| 5,244,458 A | * | 9/1993 | Takasu .................. 604/22 |
| 5,382,244 A | * | 1/1995 | Telang ................. 604/319 |
| 5,678,564 A | | 10/1997 | Lawrence et al. |
| 5,894,608 A | | 4/1999 | Birbara |
| 6,849,065 B2 | | 2/2005 | Schmidt et al. |
| 7,018,366 B2 | | 3/2006 | Easter |
| 7,220,250 B2 | | 5/2007 | Suzuki et al. |
| 2005/0279359 A1 | * | 12/2005 | LeBlanc et al. ......... 128/207.14 |
| 2009/0025717 A1 | * | 1/2009 | Pinel ................. 128/202.16 |

* cited by examiner

*Primary Examiner* — Melanie Hand
*Assistant Examiner* — Joshua Lee
(74) *Attorney, Agent, or Firm* — Edward W. Callan

(57) ABSTRACT

A urine collection device and a moisture-wicking article for use in a system for transporting urine voided from a person or an animal by collecting the urine in a moisture-wicking article that is disposed in contact with a region surrounding an urethral, opening, and drawing the urine into the collection device from the moisture-wicking article. The urine collection device includes a container defining an empty chamber for collecting urine. An elongated exterior of the container is configured and dimensioned for enabling a moisture-wicking article to be secured over the array of openings of the container by wrapping the article over the array and securing the wrapped article, and for enabling a said secured moisture-wicking article to be disposed in contact with the region of a female body surrounding the urethral opening.

19 Claims, 2 Drawing Sheets

USING MOISTURE-WICKING ARTICLE WRAPPED OVER OPENINGS IN AN ELONGATED URINE COLLECTING CONTAINER FOR DRAWING URINE FROM A REGION SURROUNDING AN URETHRAL OPENING

BACKGROUND OF THE INVENTION

The present invention pertains to collecting and transporting urine away from the body of a person or an animal during various circumstances.

A system for transporting urine voided from a person's body is described in U.S. Pat. No. 4,747,166 to Kuntz. This system includes a pad containing a core of moisture-absorbent material, a urine collection vessel, a first tube for transporting urine from the pad to the urine collection vessel, a vacuum pump and a second tube that couples the vacuum pump to the urine collection vessel. The pad is configured to make direct contact with the region of a female person's body surrounding the urethral opening and facilitates the positioning of the pad to the body surface so that urine that is expelled by the person is passed into and absorbed by the moisture-absorbent material. The moisture-absorbent material is formed with a central bore extending longitudinally of the pad along the major extent thereof. A perforated end portion of a tube is inserted into the bore.

Upon being energized, the vacuum pump applies a slight vacuum via the first and second tubes to the bore of the pad so that as the person voids, urine is drawn through openings in an outer cover layer of the pad into the moisture-absorbent material core of the pad within which the urine moves to the central bore of the pad by capillary action and by the effect of the pressure differential that exists between the inside and the outside of the pad. Once the urine reaches the central bore, the urine is drawn into the first tube through the perforation in the first tube and thence transported to the collection vessel. In one embodiment, the collection vessel and the manner in which the tubes are coupled thereto are such that urine from the urine collection vessel is not drawn into the second tube; and the urine drawn through the first tube is left in the urine collection vessel. The outer cover layer of the pad is of hydrophobic nature so that the feeling of wetness is reduced shortly after voiding has occurred.

Other systems and methods for collecting and transporting urine away from a person's body are described in U.S. Pat. Nos. 4,610,675 to Triunfol; 5,678,564 to Lawrence et al.; 5,894,608 to Birbara; 6,849,065 to Schmidt et al.; 7,018,366 to Easter and 7,220,250 to Suzuki et al.

SUMMARY OF THE INVENTION

The present invention provides a urine collection device for use in a system for transporting wine voided from a person or an animal by drawing the urine into a moisture-wicking article that is disposed in contact with a region of the person or animal surrounding an urethral opening, and further drawing the urine into the collection device from the moisture-wicking article, comprising: a container defining a chamber for collecting urine, wherein the container is closed, except for having an array of openings through which urine can be drawn into the chamber and at least one outlet port through which urine can be drawn away from the chamber; and wherein an elongated exterior of the container is configured and dimensioned for enabling a moisture-wicking article to be secured over the array of openings of the container by wrapping the article over the array and securing the wrapped article, and for enabling a said secured moisture-wicking article to be disposed in contact with the region of a female body surrounding the urethral opening.

The present invention also provides a method of transporting urine voided from the person or an animal, comprising the steps of:

(a) providing a urine collection device that includes a container defining a chamber for collecting urine, wherein the container is closed, except for having an array of openings through which urine can be drawn into the chamber and at least one outlet port through which urine can be drawn away from the chamber, and wherein the exterior of the container is configured for enabling a moisture-wicking article to be secured over the array of openings;

(b) securing a moisture-wicking article over the array of openings by wrapping the article over the array and securing the article;

(c) disposing the secured moisture-wicking article in contact with a region of the person or animal surrounding an urethral opening so that urine from the urethral opening is drawn into the moisture-wicking article; and (d) drawing the urine from the moisture-wicking material through the array of openings and into the chamber from the disposed moisture-wicking article.

The present invention further provides a moisture-wicking article adapted for use with a urine collection device for use in a system for transporting urine voided from a body of a person or an animal by drawing the urine into the moisture-wicking article when said article is disposed in contact with a region of the body surrounding the urethral opening, and drawing the urine into the collection device from the Moisture-wicking article, wherein the urine collection device includes an elongated container defining a chamber that is closed at both ends for collecting urine and having an array of openings in an elongated side of the container through which urine can be drawn into the chamber and at least one outlet port through which urine can be drawn away from the chamber, and wherein the exterior of the container is configured and dimensioned for enabling a moisture-wicking article to be secured over the array of openings of the container y wrapping the article over the array and securing the wrapped article, and for enabling a said secured moisture-wicking article to be disposed in contact with the region of the body surrounding the urethral opening.

The present invention is particularly useful for persons or animals during various circumstances. These circumstances include a condition such as incontinence or a disability that limits or impairs mobility. These circumstances also include restricted travel conditions, such as sometimes experienced by pilots, drivers, workers in hazardous areas, etc. These circumstances further include collection of urine for monitoring purposes or clinical testing.

Additional features of the present invention are described with reference to the detailed description.

DETAILED DESCRIPTION

Figure 1:
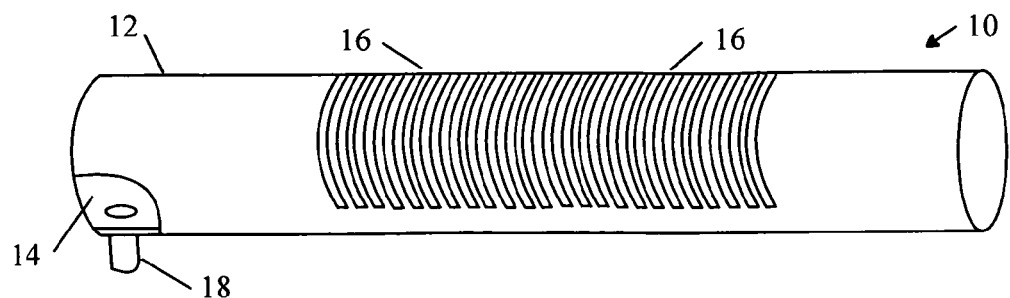
FIG. 1 is a view of one embodiment of a urine collection device according to the present invention, with some of the container having been cut away to expose a portion of the chamber and the entry into the outlet port from the chamber.

Referring to FIG. 1, one embodiment of a urine collection device 10 according to the present invention is configured for use with females. The device 10 includes a container 12, which defines a chamber 14 for collecting urine. The container 12 is closed, except for having an array of openings 16 through which urine can be drawn into the chamber 14 and at least one outlet port 18 through which urine can be drawn away from the chamber 14. Preferably, the chamber 14 is empty in order to enhance the flow rate of urine through the chamber 14.

The container 12 is made of plastic, is rigid, has an approximately cylindrical shape and is sealed at both ends. In alternative embodiments (not shown) the container 12 has some other shape and/or is not rigid and/or is made of a material other than plastic, such as aluminum or a composite of plastic and aluminum and/or some other metal.

In alternative embodiments, the array of openings 16 in the container 12 are slotted perforations, as shown in FIG. 1, openings in a porous material such as frits in a porous glass container, or openings in a mesh screen in the wall of the container. The openings may have many different arrays, shapes and spacings alternative to those of the openings 16 shown in FIG. 1.

The exterior of the container 12 is configured for enabling a moisture-wicking article 20 to be secured over the array of openings 16 and for enabling the secured moisture-wicking article 20 to be disposed in contact with the region of a female body surrounding the urethral opening.

Preferably, the array of openings 16 extends throughout an area that is somewhat larger than the area of the moisture-wicking article 20 that is immediately wetted by urine flow from the urethral opening. The area throughout which the array of openings 16 extends should not be too much larger than the immediately wetted area; otherwise excessive air flowing into the chamber 14 reduces the partial vacuum within the chamber 14 and thereby the urine collection rate and the efficiency of the urine collection device 10.

Figure 2:
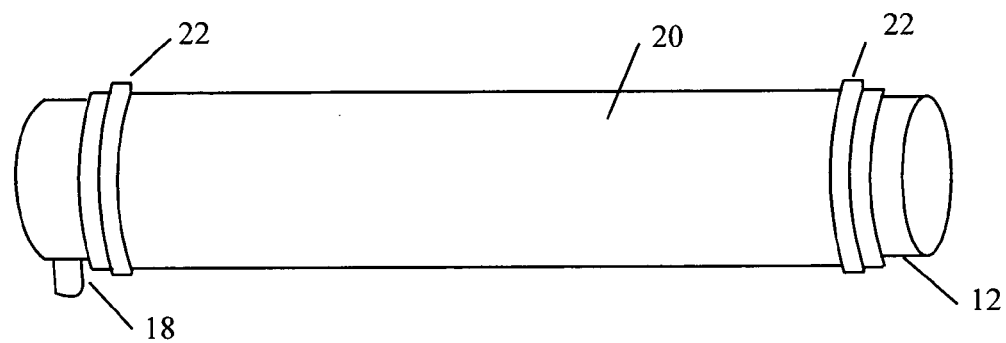
FIG. 2 illustrates securing a moisture-wicking article over the array of openings in the urine collection device shown in FIG. 1.

In the embodiment shown in FIG. 1, the container 12 is configured for enabling the moisture-wicking article 20 to be secured over the array of openings 16 by applying elastic bands 22 about the moisture-wicking article 20 at positions that are adjacent opposite ends of the array of openings 16, as shown in FIG. 2. In this embodiment, the moisture-wicking article 20 is dimensioned for being secured over the array of openings 16. In alternative embodiments, the moisture-wicking article 20 is otherwise dimensioned.

In one or more alternative embodiments (not shown), the container is configured for enabling a moisture-wicking article to be secured over the array of openings by the use of means other than elastic bands. For example, the moisture wicking article can be secured to the container by such means as spring clips, with water-resistant adhesive tape, Velcro fasteners, zippers, and snaps. Alternatively, the moisture-wicking article is in the form of a sock or sleeve that slips snugly over the container.

The moisture-wicking article 20 includes a rapidly permeable material such as gauze, felt, terrycloth, thick tissue paper, paper towel, etc. A high absorption and permeation rate is essential to allow rapid absorption and transport of urine. In one embodiment, the moisture-wicking article 20 has the moisture-wicking characteristic of a paper towel.

In an alternative embodiment (not shown), a urine collection device according to the present invention is configured for use with males. In this embodiment, the container defines a chamber for collecting urine, the container has an array of openings through which urine can be drawn into the chamber and at least one outlet port through which urine can be drawn away from the chamber, the exterior of the container is configured for enabling a moisture-wicking article to be secured over the array of openings of the container and for enabling the secured moisture-wicking article to be disposed in contact with and surrounding the region of the penis surrounding the urethral opening, and the container is made of a flexible, conformable material.

Figure 3:
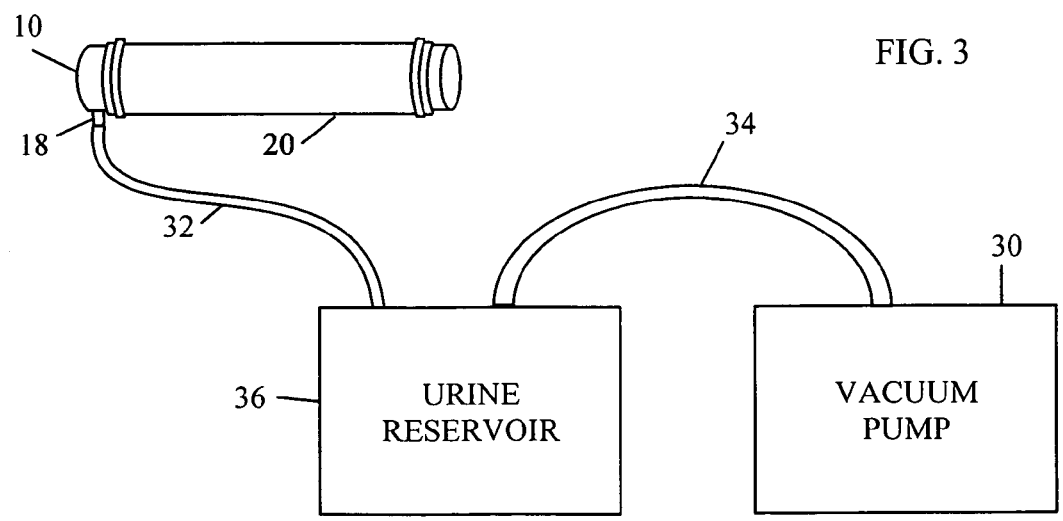
FIG. 3 is a block diagram showing the use of a urine collection device according to the present invention in one embodiment of a system for collecting and transporting urine away from the body of a person or an animal.

Referring to FIG. 3, one embodiment of a system for transporting urine voided from a person or an animal in accordance with the method of the present invention includes a urine collection device 10, a moisture-wicking article 20, a vacuum pump 30, a first flexible tube 32, a second flexible tube 34 and a urine reservoir 36. The embodiments of the urine collection device 10 and the moisture-wicking article 20 used in this system are in accordance with the present invention as described above.

The first flexible tube 32 is coupled between the outlet port 18 of the urine collection device 10 and the urine reservoir 36. The second flexible tube 34 is coupled between the urine reservoir 36 and the vacuum pump 30. The vacuum pump 30 is adapted for applying a partial vacuum to the outlet port 18 of the urine collection device 10 via the second flexible tube 34, the urine reservoir 36 and the first flexible tube 32 to thereby cause urine collected in the moisture-wicking article 20 to be drawn through the array of openings 16 in the urine collection device 10 and into the chamber 14 of the urine collection device 10, and thence to be drawn away from the chamber 14 through the outlet port 18 and the first flexible tube 32 and into the urine reservoir 36.

The vacuum pump 30 should have a sufficiently high vacuum strength and air volume transport rate such that air and liquid aspiration over the entire moisture-wicking article 20 is always rapid.

An aquarium aerator may be used as the vacuum pump 30, provided that the first flexible tube 32 is attached to the intake port of the aerator rather than to the exhaust port. Such a pump is readily available, inexpensive, relatively quiet, and designed to run continuously. The necessary static vacuum typically is about 3-10 ft. of water (10%-30% of one atmosphere; 80-250 mm Hg) with a free-flow rate of about 10-100 cubic centimeters per second. These values can vary significantly based upon the size of the body and the expected rate of urine flow.

The vacuum pump 30 may be powered by electrical AC or DC power. DC power is necessary for mobile applications, such as when a person or an animal using the urine collection device is being transported in a wheel chair or a motor vehicle or is away from an AC power source.

In one embodiment of the method of the present invention, the moisture-wicking article 20 is secured over the array of openings 16 in the container of the urine collection device 10 by wrapping the article 20 around the device 10 and applying elastic bands 22, such as rubber bands, about the moisture-wicking article 20 at opposite ends of the array of openings 16, as shown in FIG. 2.

The urine collection device 10 having the secured moisture-wicking article 20 secured thereto is then disposed so that the secured moisture-wicking article 20 is in contact with the region of the body surrounding the urethral opening. For a female, the secured moisture-wicking article 20 is placed between the legs and held snugly against the external urethra by the pressure of the legs or by such means as an undergarment, elastic strips and/or adhesive tape. For a male, the secured moisture-wicking article is secured around the penis.

The urine collection device 10 is so disposed that the outlet port 18 is at the lowest location so that the urine is quickly drawn away from the chamber 14, rather than accumulating in a pool within the chamber 14.

Urine voided from the urethral opening is collected in the moisture-wicking article 20 when the moisture-wicking article 20 is disposed in contact with the region of the body surrounding the urethral opening.

The partial vacuum applied to the outlet port 18 by the vacuum pump 30 causes urine collected in the moisture-wicking article 20 to be drawn through the array of openings 16 in the urine collection device 10 and into the chamber 14 of the urine collection device 10, and thence to be drawn away from the chamber 14 through the outlet port 18 and the first flexible tube 32 and into the urine reservoir 36.

Figure 4:
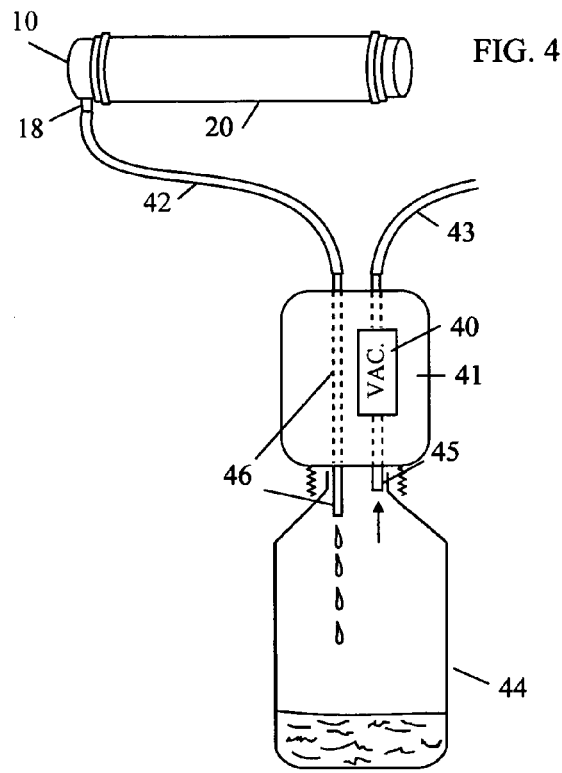
FIG. 4 is a block diagram showing the use of a urine collection device according to the present invention in a compact embodiment of a system for collecting and transporting urine away from the body of a person or an animal.

Referring to FIG. 4, a compact embodiment of a system for transporting urine voided from a person or an animal in accordance with the method of the present invention includes a urine collection device 10, a moisture-wicking article 20, a vacuum pump 40, a first flexible tube 42, a second flexible tube 43 and a replaceable urine reservoir 44. The embodiments of the urine collection device 10 and the moisture-wicking article 20 used in this embodiment are in accordance with the present invention as described above.

The chassis 41 for the vacuum pump 40 is disposed to cover an opening at the top of the urine reservoir 44 so that an air inlet 45 to the vacuum pump 40 and the lower end of a pipe 46 that extends through the chassis 41 are located within the top portion of the reservoir 44. The first flexible tube 42 is coupled between the outlet port 18 of the urine collection device 10 and the upper end of the pipe 46. The second flexible tube 43 is coupled to the air outlet port of the vacuum pump 40.

The vacuum pump 40 is adapted for applying a partial vacuum within the top portion of the reservoir 44 to thereby cause urine collected in the moisture-wicking article 20 to be drawn through the array of openings 16 in the urine collection device 10 and into the chamber 14 of the urine collection device 10, and thence to be drawn away from the chamber 14 through the outlet port 18, the flexible tube 42 and the pipe 46 and into the urine reservoir 44.

The vacuum pump 40 has the same properties as the vacuum pump 30 described above with reference to the embodiment of the system shown in FIG. 3.

The container of the urine collector device may have a shape other than the shape of the container 12 shown in FIG. 1. Examples of alternative container shapes are illustrated in FIGS. 5, 6 and 7.

Figure 5:
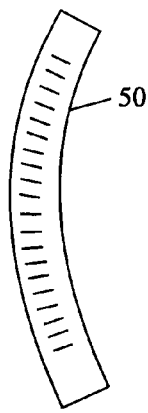
FIG. 5 illustrates an alternative shape of the container of the urine collection device shown in FIG. 1.

Referring to FIG. 5, the container 50 has a curved shape to enhance a close fit of the container 50 to the region surrounding the urethral region of a female body.

Figure 6:
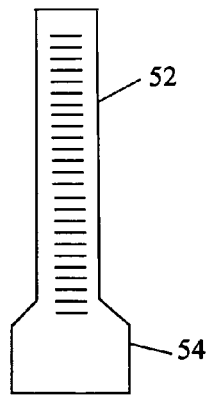
FIG. 6 illustrates another alternative shape of the container of the urine collection device shown in FIG. 1.

Referring to FIG. 6, the container 52 has a shape that is distinguished by being larger at one end 54 to enhance collection of urine.

Figure 7:
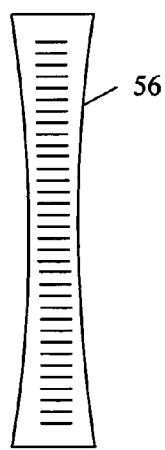
FIG. 7 illustrates still another alternative shape of the container of the urine collection device shown in FIG. 1.

Referring to FIG. 7, the container 56 has an hourglass shape to enhance a close fit of the container 56 to the region surrounding the urethral region of a female body and to enhance collection of urine. Other container shapes also may be applicable.

Figure 8:
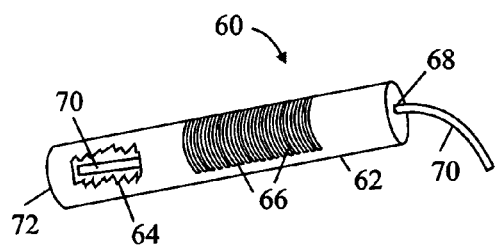
FIG. 8 is a view of an alternative embodiment of a urine collection device according to the present invention, with some of the container having been cut away to expose a portion of the chamber and a tube extending through the outlet port and into the chamber.

Referring to FIG. 8, another alternative embodiment of a urine collection device 60 according to the present invention includes a container 62, which defines an internal chamber 64 for collecting urine. The container 62 is closed, except for having an array of openings 66 through which urine can be drawn into the chamber 64 and at least one outlet port 68 through which urine can be drawn away from the chamber 64. The outlet port 68 is located in one end of the container 62 so that a urine-transfer tube 70 inserted through the outlet port 68 can readily extend within the internal chamber 64 to the opposite end 72 of the container 62. This embodiment is particularly useful when the user is wearing clothing, such as an undergarment, and/or is covered with a blanket, in that the opposite end 72 of the container 62 can be positioned conveniently at a lower elevation than the remainder of the container so that the urine-transfer tube 70 is positioned for receiving the voided urine that collects in the lowest portion within the chamber 64. The chamber 64 is empty when the urine-transfer tube 70 is not positioned within the chamber 64.

In an alternative embodiment (not shown), the urine collection device and the moisture-wicking material are integrated in a unitary composite structure. In one example of such an integrated unitary composite structure, a moisture-wicking felt layer is bonded onto the surface of the container over the array of openings in the container. In another example of such an integrated unitary composite structure, the moisture-wicking function is provided by a fritted wall of a porous glass container.

Different embodiments of the urine collection device according to the invention are configured for both adult and pediatric applications and for veterinary applications for animals of different species and sizes.

The benefits specifically stated herein do not necessarily apply to every conceivable embodiment of the present invention. Further, such stated benefits of the present invention are only examples and should not be construed as the only benefits of the present invention.

While the above description contains many specificities, these specificities are not to be construed as limitations on the scope of the present invention, but rather as examples of the preferred embodiments described herein. Other variations are possible and the scope of the present invention should be determined not by the embodiments described herein but rather by the claims and their legal equivalents.

The invention claimed is:

1. A urine collection device for use in a system for transporting urine voided from a person or an animal by drawing the urine into a moisture-wicking article that is disposed in contact with a region of the person or animal surrounding an urethral opening, and further drawing the urine into the collection device from the moisture-wicking article, comprising:
    a container defining a chamber for collecting urine,
    wherein the container is closed, except for having an array of openings through which urine can be drawn into the chamber and at least one outlet port through which urine can be drawn away from the chamber; and wherein an elongated exterior of the container is configured and dimensioned for enabling a moisture-wicking article to be secured over the array of openings of the container by wrapping the article over the array and securing the wrapped article, and for enabling said secured moisture-wicking article to be disposed in contact with the region of a female body surrounding the urethral opening.

2. A device according to claim 1, wherein the chamber is empty.

3. A device according to claim 1 in combination with said moisture-wicking article when the moisture-wicking article is wrapped and secured over the array of openings, wherein the moisture-wicking article is dimensioned for being secured over the array of openings.

4. A combination according to claim 3, wherein the moisture-wicking article has the moisture-wicking characteristic of a paper towel.

5. A combination according to claim 1, wherein the moisture-wicking article has the moisture-wicking characteristic of a paper towel.

6. A combination according to claim 1, in further combination with a vacuum pump for drawing the urine through the array of openings and into the chamber from the disposed moisture-wicking article.

7. A combination according to claim 6, wherein the vacuum pump is disposed for drawing the urine away from the chamber through the outlet port.

8. A combination according to claim 7, wherein the vacuum pump is disposed for applying a partial vacuum to the outlet port.

9. A device according to claim 1, wherein the container is made of plastic, is rigid, has a cylindrical shape and is sealed at both ends.

10. A method of transporting urine voided from a person or an animal, comprising the steps of:
  (a) providing a urine collection device that includes a container defining a chamber for collecting urine, wherein the container is closed, except for having an array of openings through which urine can be drawn into the chamber and at least one outlet port through which urine can be drawn away from the chamber, and wherein the exterior of the container is configured for enabling a moisture-wicking article to be secured over the array of openings;
  (b) securing a moisture-wicking article over the array of openings by wrapping the article over the array and securing the article;
  (c) disposing the secured moisture-wicking article in contact with a region of the person or animal surrounding an urethral opening so that urine from the urethral opening is drawn into the moisture-wicking article; and
  (d) drawing the urine from the moisture-wicking material, through the array of openings and into the chamber from the disposed moisture-wicking article.

11. A method according to claim 10, wherein step (a) comprises the step of:
  (e) providing said collection device in which the chamber is empty.

12. A method according to claim 10, further comprising the step of:
  (e) drawing the urine away from the chamber through the outlet port.

13. A method according to claim 12, wherein steps (d) and (e) comprise the step of
  (f) applying a partial vacuum to the outlet port.

14. A method according to claim 13, wherein the moisture-wicking article is dimensioned for being secured over the array of openings and has the moisture-wicking characteristic of a paper towel.

15. A method according to claim 10, wherein the moisture-wicking article is dimensioned for being secured over the array of openings and has the moisture-wicking characteristic of, a paper towel.

16. A method according to claim 10, wherein step (a) comprises the step of:
  (e) providing said container that is made of plastic, is rigid, has a cylindrical shape and is sealed at both ends.

17. A moisture-wicking article adapted for use with a urine collection device for use in a system for transporting urine voided from a body of a person or an animal by drawing the urine into the moisture-wicking article when said article is disposed in contact with a region of the body surrounding the urethral opening, and drawing the urine into the collection device from the moisture-wicking article, wherein the urine collection device includes an elongated container defining a chamber that is closed at both ends for collecting urine and having an array of openings in an elongated side of the container through which urine can be drawn into the chamber and at least one to outlet port through which urine can be drawn away from the chamber, and wherein the exterior of the container is configured and dimensioned for enabling a moisture-wicking article to be secured over the array of openings of the container by wrapping the article over the array and securing the wrapped article, and for enabling a said secured moisture-wicking article to be disposed in contact with the region of the body surrounding the urethral opening.

18. A moisture-wicking article according to claim 17, wherein the article is dimensioned for being secured over the array of openings by the application of elastic bands about the moisture-wicking article at opposite ends of the array of openings.

19. A moisture-wicking article according to claim 17, wherein the article has the moisture-wicking characteristic of a paper towel.

* * * * *